US009522168B2

(12) United States Patent
Bonner et al.

(10) Patent No.: US 9,522,168 B2
(45) Date of Patent: Dec. 20, 2016

(54) **TOPICAL COMPOSITIONS COMPRISING *ACMELLA OLERACEA* EXTRACTS AND USES THEREOF**

(71) Applicant: JOHNSON & JOHNSON CONSUMER INC., Skillman, NJ (US)

(72) Inventors: Patricia Bonner, Branchburg, NJ (US); Alexandria Dinapoli Marzano, Staten Island, NY (US); Claudia Kaminski, Milford, NJ (US); Kurt A. Reynertson, Hopewell, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/290,015

(22) Filed: May 29, 2014

(65) Prior Publication Data

US 2015/0343006 A1 Dec. 3, 2015

(51) Int. Cl.
| | |
|---|---|
| *A61K 36/00* | (2006.01) |
| *A61K 36/28* | (2006.01) |
| *A61K 9/00* | (2006.01) |
| *A61K 36/14* | (2006.01) |
| *A61K 36/185* | (2006.01) |

(52) U.S. Cl.
CPC ............ *A61K 36/28* (2013.01); *A61K 9/0014* (2013.01); *A61K 36/14* (2013.01); *A61K 36/185* (2013.01)

(58) Field of Classification Search
None
See application file for complete search history.

(56) References Cited

U.S. PATENT DOCUMENTS

| | | | |
|---|---|---|---|
| 6,090,811 A | 7/2000 | Jacobs et al. | |
| 6,280,754 B1 * | 8/2001 | Hanada | A61K 8/34 424/401 |
| 7,442,391 B2 | 10/2008 | Koganov | |
| 7,473,435 B2 | 1/2009 | Koganov | |
| 7,537,791 B2 | 5/2009 | Koganov | |
| 2009/0227683 A1 | 9/2009 | Liebel et al. | |
| 2011/0081393 A1 | 4/2011 | Komatsuki et al. | |
| 2011/0171288 A1 * | 7/2011 | Mohammadi | A61K 8/0295 424/450 |
| 2012/0027697 A1 | 2/2012 | Deo | |

FOREIGN PATENT DOCUMENTS

| | | | |
|---|---|---|---|
| JP | 2004189660 A | | 7/2004 |
| JP | 2004189660 A | * | 7/2004 |
| JP | 2004189660 A | | 3/2005 |
| JP | 2005075827 A | | 3/2005 |
| JP | 2005343795 A | | 12/2005 |
| WO | WO2005115325 A1 | | 12/2005 |
| WO | WO2006099707 A1 | | 9/2006 |
| WO | WO2009123355 A2 | | 10/2009 |
| WO | WO2010010394 A2 | | 1/2010 |
| WO | WO2011158964 A1 | | 12/2011 |
| WO | WO2013002421 A1 | | 1/2013 |

OTHER PUBLICATIONS

Guimaraes, Terpenes and derivatives as a new perspective for pain treatment: A patent review. Expert Opinion on Therapeutic Patents, (Mar. 2014) vol. 24, No. 3, pp. 243-265.*
Tapondjou et al, Bioactivities of cymol and essential oils of Cupressus sempervirens and Eucalyptus saligna against Sitophilus zeamais Motschulsky and Tribolium confusum du Val. Journal of Stored Products Research (2005), 41(1), 91-102.*
Boonen et al, "LC-MS Profiling of N-alkylamides in *Spilanthes acmella* Extract and the Transmucosal Behaviour of its Main Bio-active Spilanthol", *Journal of Pharmaceutical and Biomedical Analysis* (2010) 53:243-249.
Boonen et al, "Transdermal Behaviour of the N-alkylamide Spilanthol (Affinin) from *Spilanthes acmella* (Compositae) Extracts", *Journal of Ethnopharmacology* (2010) 127:77-84.
Chakraborty et al, "Preliminary Studies on Local Anesthetic and Antipyretic Activities of *Spilanthes acmella* Murr. in Experimental Animal Models", *Indian Journal of Pharmacology* (2010) 42(5):227-279. (Abstract).
Crouch et al, "A Novel Alkylamide from the Leaves of Acmella Caulirhiza (Asteraceae), a Traditional Surface Analgesic", *South African Journal of Botany* (2005) 71(2):228-230.
De Spiegeleer et al, "Skin Penetration Enhancing Properties of the Plant N-alkylamide Spilanthol", *Journal of Ethnopharmacology* (2013) 148:117-125.
Deciga-Campos et al, "Antinociceptive Effect of *Heliopsis longipes* Extract and Affinin in Mice", *Planta Medica* (2010) 76(7):665-670.
Deciga-Campos et al, "Pharmacological and Toxicological Profile of Extract from *Heliopsis longipes* and Affinin", *Drug Development Research* (2012) 73:130-137.
Dias et al, "Spilanthol from Spilanthes Acmella Flowers, Leaves and Stems Obtained by Selective Supercritical Carbon Dioxide Extraction", *Journal of Supercritical Fluids* (2012) 61:62-70.
Hernandez et al, "Anti-inflammatory Effects fo Ethanolic Extract and Alkamides-derived from *Heliopsis longipes* Roots", *Journal of Ethnopharmacology* (2009) 124:649-652.
Inoue et al, "Profile of Capsaicin-induced Mouse Ear Oedema as Neurogenic Inflammatory Model: Comparison with Arachidonic Acid-Induced Ear Oedema", *British Journal of Pharmacology* (1993) 110(4):1614-1620.
International Cosmetic Ingredient Dictionary and Handbook, 7th Edition (1997) Editors John A. Wenninger and G. N., McEwen, Jr., Published by the Cosmetic, Toiletry, and Fragrance Association, Washington DC, pp. 1626, 1654-1661, 1673-1686, and 1693-1697.
Lawson, "Potassium Channel Openers as Potential Therapeutic Weapons in Ion Channel Disease", *Kidney International* (2000) 57:838-845.
Leng et al, "Detection of Bioactive Compounds from *Spilanthes acmella* (L.) Plants and its Various in vitro Culture Products", *Journal of Medicinal Plants Research* (2011) 5(3):371-378. (Abstract).

(Continued)

Primary Examiner — Qiuwen Mi
(74) Attorney, Agent, or Firm — Victor Tsu

(57) ABSTRACT

Extracts of *Acmella oleracea* in combination with a terpene-containing extract selected from the group consisting of *Cupressus sempervirens* and *Cistus ladanifer* provide surprisingly improved topical analgesic properties.

6 Claims, No Drawings

(56) References Cited

OTHER PUBLICATIONS

Martin et al, "Spilanthol-related Amindes from Acmella Ciliata", *Phytochemistry* (1984) 23(8):1781-1783.
Nagashima et al, "A New Alkamide from *Spilanthes acmella* L.", *Chemistry Express* (1992) 7(2):153-156.
Nagashima et al, "Two Sesquiterpenes from *Spilanthes acmella* L.", *Chemistry Express* (1991) 6(12):993-996.
Nakatani et al, "Pungent Alkamides from *Spilanthes acmella* L. Var. Oleracea Clarke", *Biotechnology Bioscience and Biochemistry* (1992) 56(5):759-762.
Polya, *Biochemical Targets of Plant Bioactive Compounds: a Pharmacological Reference Guide to Sites of Action and Biological Effects*(2003) Table 4.3, pp. 142-146.
Prachayasittikul et al, "Bioactive Metabolites from *Spilanthes acmella* Murr", *Molecules* (2009) 14(2):850-867. (Abstract).
Ramsewak et al, "Bioactive N-isobutylamides from the Flower Buds of *Spilanthes acmella*", *Phytochemistry* (1999) 51:729-732.
Rios et al, "Analgesic Activity of Affinin, an Alkamide from *Heliopsis longipes* (Compositae)", *Journal of Ethnopharmacology* (2007) 110:364-367.
Sahu et al, "A Review on Phytopharmacology and Micropropagation of *Spilanthes acmella*", *Pharmacologyonline* (2011) 2:1105-1110.
Sci, *Horticulture Group Newsletter-Apr. 2012*, <<Jun. 17, 2014, http://www.soci.org/News/Horticulture/hort-newsletter-Apr-12.
Spelman et al, "The Traditional Medicine *Spilanthes acmella*, and the Alkylamides Spilanthol and Undeca-2E-ene-8,10-diynoic Acid Isobutylamide, Demonstrate in vitro and in vivo Anti-malarial Activity", *Phytother Res.* (2011) 25(7):1098-1101.
Takano, "Possible Antipruritic Effects of K+ Channel Openers in Mice", *Journal of Dermatological Science* (2004) 35:71-73.
Wagner et al, "In Vitro Inhibition of Arachidonate Metabolism by some Alkamies and Prenylated Phenols", *Planta medica* (1989) 55(6):566-567.
Zhang et al, "Studies on Chemical Constituents from Radix and Phizome of Asarum Longerhizomatosum", *Zhongcaoyao (Chinese Traditional and Herbal Drugs)* (2002) 33(4):297-299. (with English language Abstract).
Gupta N et al: "Design of Akkalkara 1-12 (Spilanthes acmella) formulations for antimicrobial and topical anti-inflammatoryactivities", International Journal of Pharma and Biosciences 2012 International Journal of Pharma and Bio Sciences Ind, vol. 3, No. 4, Oct. 2012 (Oct. 2012), pp. 161-170, XP55195777, ISSN: 0975-6299—the whole document.
Suchita Dubey et al: "Phytochemistry, Pharmacology and Toxicology of Spilanthes acmella: A Review", Advances in Pharmacological Sciences, vol. 2013, Jan. 1, 2013 (Jan. 1, 2013), pp. 423750/1-10, XP55195760, ISSN: 1687-6334, DOI: 10.3390/molecules14020850 tables 1, 2.
Database WPI—Week 200940 Thomson Scientific, London, GB; AN 2009-K39223—XP002740914 & JP 2004 189660 A (Hayashibara Seibutsu Kagaku) Jul. 8, 2004 (Jul. 8, 2004) abstract.
Database WPI—Week 200525—Thomson Scientific, London, GB; AN 2005-237785—XP002740915 & JP 2005 075827 A (Gattefosse SA) Mar. 24, 2005 (Mar. 24, 2005) abstract.
Smail Aazza et al: "Anti-oxidant, anti-inflammatory and anti-proliferative activities of Moroccan commercial essential oils", Natural Product Communications, vol. 9, No. 4, Apr. 1, 2014 (Apr. 1, 2014), pp. 587-594, XP55195797, US ISSN: 1934-578X—the whole document.
S.Taila et al.: Anti-inflammatory and anti-oxidant activity of six *Cistus* species II , Journal of Pharmacy and Pharmacology, vol. 60, No. Suppl. 1, 2008, pp. A62-A63, XP009184856, British Pharmaceutical Conference; Manchester, UK; Sep. 7-9, 2008—ISSN: 0022-3573—table 1.
International Search Report dated Jul. 1, 2015 for PCT/US2015/028818.

* cited by examiner

TOPICAL COMPOSITIONS COMPRISING *ACMELLA OLERACEA* EXTRACTS AND USES THEREOF

FIELD OF INVENTION

The present invention relates to compositions comprising plant extracts for use on skin. More specifically, it relates to compositions comprising extracts of *Acmella oleracea* having improved topical analgesic properties.

DESCRIPTION OF RELATED ART

Eczema, psoriasis, acne, rosacea, contact irritant dermatitis, atopic dermatitis, allergic dermatitis, sunlight-induced dermatoses, dry skin and muscle injuries are all conditions that cause itch, pain, stinging and/or burning sensations of the skin and/or muscles. Consumers have relied on analgesic agents to treat these conditions for many years. Analgesic agents reduce neurosensory sensations, such as pain, itch, sting and burning sensations, without resulting in loss of consciousness. Analgesics are sometimes referred to as painkiller medications. There are many different types of analgesic medications available in both prescription and over-the-counter preparations. Examples of analgesic drugs include aspirin, acetaminophen, ibuprofen, naproxen, the COX-2 inhibitor celecoxib, and narcotic drugs including morphine, oxycodone and hydrocodone.

Topical analgesic agents are also called counter-irritants. The name derives from the fact that these agents cause a reddening of the skin by causing the blood vessels of the skin to dilate, which gives a soothing feeling of warmth. The term counter-irritant refers to the idea that irritation of the sensory nerve endings alters or offsets pain in the underlying muscle or joints that are served by the same nerves. Examples of topical analgesic agents include capsaicin, *capsicum* oleoresin, choline salicylate, ethyl salicylate, glycol salicylate, methyl salicylate, menthol, salicylic acid and turpentine oil. Although analgesic agents are effective in relieving irritation, some have undesirable side effects. For example, some analgesics slow the heart rate of the consumer. Other analgesics are difficult to deliver topically due to skin permeability issues. There is a continuing need for compositions that provide an analgesic effect to the skin and/or muscles without the need for the use of conventional analgesic materials, thereby relieving or reducing edema, itch, pain, stinging and/or burning sensations of the skin and/or muscles while avoiding the need to use conventional analgesic materials.

*Acmella oleracea* is a member of the family Asteraceae (daisy) and genus *Acmella*. The genus *Acmella* contains about thirty species of plants, native to the Americas. *Acmella oleracea* (also known as the toothache plant) is native to Brazil, and it is cultivated worldwide for medicinal, insecticidal, and gardening purposes.

*Cistus ladanifer* is a member of the family Cistaceae and genus *Cistus*. The genus *Cistus* contains about twenty species of perennial shrubs found on dry or rocky soils throughout the Mediterranean region. It is a popular ornamental plant, and it is also a source of rock rose oil.

*Cupressus sempervirens* is a member of the family Cupressaceae and genus *Cupressus*. The genus *Cupressus* contains about 15-25 species of trees having the common name "cypress". *Cupressus sempervirens* is a medium-sized evergreen tree native to the eastern Mediterranean region. It is widely cultivated as an ornamental plant, and it is also a source durable, scented wood and of Italian Cypress oil.

The present invention relates to the unexpected discovery that extracts of *Acmella oleracea* in combination with a terpene-containing extract selected from the group consisting of *Cupressus sempervirens* and *Cistus ladanifer* provide surprisingly improved topical analgesic properties.

SUMMARY OF THE INVENTION

Applicants have discovered unexpectedly that extracts of *Acmella oleracea* in combination with a terpene-containing extract selected from the group consisting of *Cupressus sempervirens* and *Cistus ladanifer* provide surprisingly improved topical analgesic properties.

In particular, applicants have tested *Acmella oleracea* extracts and have discovered that such extracts exhibit significant and unexpected improved topical analgesic effects. More specifically, as detailed in the Examples herein, compositions including combinations of *Acmella oleracea* extracts and one or more terpene-containing extract selected from the group consisting of *Cistus ladanifer* oil, *Cupressus sempervirens* oil, and combinations thereof provided surprisingly improved topical analgesic properties.

In another aspect, the present invention relates to methods for providing topical analgesia employing combinations of *Acmella oleracea* extracts and one or more terpene-containing extract selected from the group consisting of *Cistus ladanifer* oil, *Cupressus sempervirens* oil.

DESCRIPTION OF THE INVENTION

Applicants have discovered unexpectedly that extracts of *Acmella oleracea* in combination with a terpene-containing extract selected from the group consisting of *Cupressus sempervirens* and *Cistus ladanifer* provide surprisingly improved topical analgesic properties. It is believed that the *Acmella oleracea* extracts include alkamides, including spilanthol.

As used herein, the term "sensation-blocking agent" and variants thereof relate to agents that provide potassium ion at the area of skin to which the composition is administered, in amounts effective to provide an analgesic effect to the skin without the requirement of a conventional analgesic material.

As used herein, the term "analgesic effect" and variants thereof relate to relief or reduction of symptoms such as itching, pain, stinging or burning.

As used herein, "topically applying" and variants thereof relate to directly laying on or spreading on outer skin, e.g., by use of the hands or an applicator such as a wipe, puff, roller or spray.

As used herein, the term "cosmetically-acceptable" and variants thereof relates means that the product(s), compound(s), or composition(s) which the term describes are suitable for use in contact with tissue of a mammal (e.g., the skin or hair) without undue toxicity, incompatibility, instability, irritation, allergic response, and the like. This term is not intended to limit the compound/product/composition to which it describes for use solely as a cosmetic, e.g., the ingredient/product may be used as a pharmaceutical.

As used herein, the term "cosmetically/dermatologically acceptable carrier" means a carrier that is suitable for use in contact with the skin without undue toxicity, incompatibility, instability, irritation, allergic response, and the like.

As used herein, the term "emollient" and variants thereof relate to materials used for the prevention or relief of dryness, as well as for the protection, of the skin. A wide variety of suitable emollients is known and may be used herein. See International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "INCI Handbook").

As used herein, unless otherwise specified, all percentages of ingredients in compositions are weight percent of active/solids ingredient based on the total weight of composition.

Extracts of *Acmella oleracea*

Any suitable extracts of the whole plant, flower, stem, leaves and/or roots of *Acmella oleracea* may be used in accord with the present invention. Suitable extracts may be derived from live or dried plant, small cuttings or other portions thereof, and the like.

*Acmella oleracea* extracts containing alkamides, including spilanthol are commercially available from a variety of different sources. For example, an extract of *Acmella oleracea* is available from GATTEFOSSE CORPORATION, Plaza I, 115 West Century Road, Suite 340, Paramus, N.J., USA 07652 under the tradename Gatuline® Expression.

While spilanthol and other compounds can be extracted from the whole plant, the flower is understood to have the highest concentration of these desirable compounds (Ref: Dias, A. M. A.; Santos, P.; Seabra, I. J.; Junior, R. N. C.; Braga, M. E. M.; de Sousa, H. C.). Spilanthol from *Spilanthes acmella* (also known as *Acmella oleracea*) flowers, leaves and stems can be used to obtain an *Acmella oleracea* extract by selective supercritical carbon dioxide extraction (Ref: Journal of Supercritical Fluids (2012), 61, 62-70). Alternatively, suitable extracts of *Acmella oleracea* whole plant, flower, stem, leaves and/or roots may be obtained using conventional methods including, but not limited to, direct extraction of material from the biomass by grinding, macerating, pressing, squeezing, mashing, centrifuging, and/or processes such as cold percolation, agitation/distillation, microwave assisted extraction, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. Any of a variety of solvents including polar solvents, non-polar solvents, or combinations of two or more thereof may be used in methods of comprising solvent extraction. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids.

Extracts of *Cistus ladanifer*

Any suitable extracts of the whole plant, flower, stem, leaves and/or seed of *Cistus ladanifer* may be used in accord with the present invention. Suitable extracts may be derived from live or dried plant, small cuttings or other portions thereof, and the like.

*Cistus ladanifer* extracts containing terpenes are commercially available from a variety of different sources. For example, an extract of *Cistus ladanifer* is available from Excellentia International (Edison, N.J., USA), under the tradename Ciste oil.

Extracts of *Cupressus sempervirens*

Any suitable extracts of the whole plant, flower, stem, leaves and/or seed of *Cupressus sempervirens* may be used in accord with the present invention. Suitable extracts may be derived from live or dried plant, small cuttings or other portions thereof, and the like.

*Cupressus sempervirens* extracts containing terpenes are commercially available from a variety of different sources. For example, an extract of the leaves and branches of *Cupressus sempervirens* is available from Excellentia International (Edison, N.J., USA), under the tradename Cypress oil.

While it is known that *Acmella oleracea* extracts containing spilanthol have some minor analgesic properties, it is heretofore unknown that these properties can be synergistically enhanced by combining the *Acmella oleracea* extracts with extracts of *Cistus ladanifer* or *Cupressus sempervirens*, or combinations of both.

In particular, the *Acmella oleracea* extracts have a baseline biological analgesic effect. The extracts of *Cistus ladanifer* and *Cupressus sempervirens* also show some limited analgesic effect.

Combining the extracts may be expected to have an additive effect. This would be the case if a specific dose of *Acmella oleracea* extracts gives a result of "1", and a specific dose of either of the terpene-containing extracts gives a result of "1". The combination may be expected to provide a result of "2". Typically this is the case when *Acmella oleracea* and the terpene-containing extracts are acting in different pathways to achieve the same result, or if the dose of *Acmella oleracea* and the terpene-containing extracts is low enough that combining them will give you more activity.

Another possibility is when the biological process initiated by the *Acmella oleracea* extract simply cannot be "turned on" any further. This is typically the case when the two compositions affect the same biological target, and there is no further ability to "turn on" the biological process.

However, we have discovered that the particular terpene-containing extracts of *Cistus ladanifer* and *Cupressus sempervirens* combine synergistically with the *Acmella oleracea* extract to unexpectedly enhance the combined analgesic properties. These unexpected results are shown in the Examples section, below.

The terpene compounds present in the extracts of *Cistus ladanifer* and *Cupressus sempervirens* may include, but are not limited to, α-pinene, β-pinene, viridiflorol, bornyl acetate, 1,8-cineole, camphene, sabinene, myrcene, α-phellandrene, α-terpinene, γ-terpinene, limonene, p-cymene, 1,8-cineol, 2,2,6-trimethylcyclohexanone, fenchone, α-thujone, isomenthone, benzaldehyde, acetophenone, cis-citral, trans-citral, geranyl acetate, cis-3-hexen-1-ol, trans-2-hexen-1-ol, linalool, terpinen-4-ol, borneol, α-terpineol, nerol, geraniol, eugenol, 3-carene, α-terpinyl acetate, α-terpinolene, cedrol, manoyle oxide and combinations thereof.

The *Cistus ladaniferus* and *Cupressus sempervirens* extracts may be-obtained through steam distillation or solvent extraction of the upper parts of the plants as described for *Acmella oleracea*, above.

The composition includes a combination of about 0.1% to about 19% by weight of the total composition of the extract of *Acmella oleracea* and about 0.1% to about 19% by weight of the total composition of the extract of *Cistus ladanifer* and *Cupressus sempervirens*.

In addition, the compositions of the present invention may also contain a sensation-blocking agent. By sensation-blocking agent, it is meant that such agent provides potassium ion at the area of skin to which the composition is administered, in amounts effective to provide an analgesic effect to the skin without the requirement of a conventional analgesic material, whether the potassium ion is delivered directly to the area of the skin by administration of the composition thereto, or by generation of the potassium ion at the area of skin to which the composition is administered. Such agent may be selected from the group consisting of potassium salts and potassium channel agonists. Potassium salts may be used to deliver potassium ion to the site of the skin exhibiting symptoms, while potassium channel agonists permit potassium ions to be generated at the site of the skin exhibiting symptoms. The amount of sensation-blocking agent in the compositions of the present invention is effective to provide potassium ion in the composition at a range of from about 0.25% to about 10%, for example from about 0.75% to about 2%, by weight of the composition.

Suitable potassium salts include, but are not limited to, potassium lactate, potassium bromide, potassium carbonate, potassium chlorate, potassium chloride, potassium chromate, potassium cyanide, potassium dichromate, potassium iodide, potassium nitrate, potassium sulfate, potassium pyrophosphate, potassium fluorosilicate and potassium sodium tartrate.

Suitable potassium channel agonist include, without limitation, a chemically diverse group of agents such as minoxidil, pinacidil, diazoxide, cromakalin, nicorandil, and aprikalim. (See Lawson, 2000; Takano et. al., 2004, and those listed in table 4.3 of Biochemical Targets of Plant Bioactive Compounds, Polya, 2003). While not intending to be limited by the following, potassium channel agonists induce an efflux of potassium from the cells. This creates a hyperpolarized state that restricts calcium from entering back into the cells and dampens cellular excitability. Potassium channel agonists also affect neurons by decreasing neuronal excitability and interfering with neurotransmission. Itch, pain, sting and burning sensations are transmitted by sensory neurons such as unmyelinated C-fibers. Thus, the effects of potassium channel agonists on neurotransmission inhibit these neurosensory sensations.

The compositions of the present invention may also include an amine compound. Suitable amine compounds include, but are not limited to dimethylethanolamine ("DMEA") and tetrahydroxypropyl ethylenediamine. The amount of amine compound may range from about 1% to about 5% or about 2.5% by weight of the total composition.

The compositions of the present invention are prepared by standard techniques well known to those skilled in the art. If the composition comprises more than one phase, in general the different phases will be prepared separately, with materials of similar phase partitioning being added in any order. The two phases will then be combined with vigorous stirring to form the multiphase system, e.g., an emulsion or dispersion. Any ingredients in the formulation with high volatility, or which are susceptible to hydrolysis at high temperatures, will usually be added post-mixing of the different phases with gentle stirring.

The compositions of the present invention are useful for relieving or reducing symptoms of itch, pain, stinging and/or burning sensations of the skin or muscles by providing an analgesic effect. By analgesic effect, it is meant that the composition, when applied to an area of skin suffering from symptoms of itch, pain, stinging or burning sensations, provides relief or reduction of such symptoms that are similar to relief or reduction of such symptoms provided by known analgesic compositions, but without the negative side effects of such known analgesic compositions. The compositions are topically applied to skin exhibiting these sensations. As used herein, "topically applying" means directly laying on or spreading on outer skin, e.g., by use of the hands or an applicator such as a wipe, puff, roller or spray. As used herein, "cosmetically-acceptable" means that the product(s), compound(s), or composition(s) which the term describes are suitable for use in contact with tissue of a mammal (e.g., the skin or hair) without undue toxicity, incompatibility, instability, irritation, allergic response, and the like. This term is not intended to limit the compound/product/composition to which it describes for use solely as a cosmetic, e.g., the ingredient/product may be used as a pharmaceutical. As used herein, "topical carrier" means one or more compatible solid or liquid filler diluents that are suitable for topical administration to a mammal. Examples of topical carriers include, but are not limited to, water, waxes, oils, emollients, emulsifiers, thickening agents, gelling agents, and mixtures thereof.

The compositions of the present invention may be provided as formulations suitable for topical application to skin. The composition may comprise a cosmetically-acceptable topical carrier. The cosmetically-acceptable topical carrier may comprise from about 50% to about 99.99%, by weight, of the composition, e.g., from about 80% to about 95%, by weight, of the composition. The compositions may be made into a wide variety of product types that include, but are not limited to, solid and liquid compositions, such as lotions, creams, gels, sticks, sprays, shaving creams, ointments, cleansing liquid washes and solid bars, shampoos, pastes, powders, mousses, shaving creams and wipes. These product types may comprise several types of cosmetically acceptable topical carriers including, but not limited to, solutions, emulsions, e.g., microemulsions and nanoemulsions, gels, solids and liposomes. The following are non-limitative examples of such carriers. Other carriers can be formulated by those of ordinary skill in the art.

The compositions of the present invention can be formulated as solutions. Solutions typically include an aqueous solvent, e.g., from about 50% to about 99.99%, or from about 90% to about 99%, of a cosmetically-acceptable aqueous solvent. Topical compositions of the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients is known and may be used herein. See International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7$^{th}$ Edition, 1997) (hereinafter "INCI Handbook").

A lotion can be made from such a solution. Lotions typically comprise from about 1% to about 20%, e.g., from about 5% to about 10%, of an emollient(s) and from about 50% to about 90%, e.g., from about 60% to about 80%, of water.

Another type of product that may be formulated from a solution is a cream. A cream typically comprises from about 5% to about 50%, e.g., from about 10% to about 20%, of an emollient(s) and from about 45% to about 85%, e.g., from about 50% to about 75%, of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in the INCI Handbook pp. 1693-1697.

The compositions of the present invention may be formulated as emulsions. If the carrier is an emulsion, from about 1% to about 10%, e.g., from about 2% to about 5%, of the carrier comprises an emulsifier(s). Emulsifiers may be nonionic, anionic or cationic. Suitable emulsifiers are disclosed in, for example, INCI Handbook, pp. 1673-1686.

Lotions and creams can be formulated as emulsions. Typically such lotions comprise from 0.5% to about 5% of an emulsifier(s). Such creams would typically comprise from about 1% to about 20%, e.g., from about 5% to about 10% of an emollient(s); from about 20% to about 80%, e.g., from 30% to about 70%, of water; and from about 1% to about 10%, e.g., from about 2% to about 5%, of an emulsifier(s).

Single emulsion skin care preparations of the oil-in-water type and water-in-oil type, such as lotions and creams, are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

The compositions of this invention can also be formulated as a gel, e.g., an aqueous gel using a suitable gelling agent(s). Suitable gelling agents for aqueous gels include, but are not limited to, natural gums, acrylic acid and acrylate polymers and copolymers, and cellulose derivatives, e.g., hydroxymethyl cellulose and hydroxypropyl cellulose. Suitable gelling agents for oils such as mineral oil include, but are not limited to, hydrogenated butylene/ethylene/styrene copolymer and hydrogenated ethylene/propylene/styrene copolymer. Such gels typically comprise between about 0.1% and 5%, by weight, of such gelling agents.

The compositions of the present invention can also be formulated into a solid formulation, e.g., a wax-based stick, soap bar composition, powder, or a wipe containing powder.

The compositions of the invention may contain, in addition to the aforementioned components, a wide variety of additional oil-soluble materials and/or water-soluble materials conventionally used in compositions for use on skin, hair, and nails at their art-established levels.

The compositions may be applied one or more times a day, for example twice a day. The amount used will vary with the age and physical condition of the end user, the duration of the treatment, the specific compound, product, or composition employed, the particular cosmetically-acceptable carrier utilized, and like factors. Several examples are described below. The invention should not be construed to be limited to the details thereof.

EXAMPLES

Several examples are described below. The invention should not be construed to be limited to the details thereof.

Example 1

Arachidonic Acid-Induced Inflammation Methodology

Arachidonic Acid-Induced Inflammation Groups of ten mice each were weighed and placed in individual Plexiglas® squares. The test article or vehicle was administered topically to the outer surface of both ears. At the end of the absorption time (30 minutes-±5 minutes and 60 minutes-±5 minutes), the arachidonic acid (left ear) and ethanol (right ear) were administered topically to the inner surface of the mouse ear. Thirty and sixty minutes (±5 minutes) after the administration of arachidonic acid and ethanol the ears were measured for thickness with a micrometer. Redness was scored based on gross observation of the ear. The results are shown in Table 1 below as % reduction versus placebo, where the lower the score, the better the efficacy.

TABLE 1

| | Formulation and Efficacy | | | | | | | | |
|---|---|---|---|---|---|---|---|---|---|
| INCI Name | 1 | 2 | 3 | 4 | 5 | 6 | 7 | 8 | 9 |
| Water | QS | QS | QS | QS | QS | QS | QS | QS | QS |
| Oatmeal | 1.00 | 1.00 | 1.00 | 1.00 | 1.00 | 1.00 | 1.00 | 1.00 | 1.00 |
| Sodium Chloride | 0.01 | 0.01 | 0.01 | 0.01 | 0.01 | 0.01 | 0.01 | 0.01 | 0.01 |
| Disteryldimonium Chloride | 5.00 | 5.00 | 5.00 | 5.00 | 5.00 | 5.00 | 5.00 | 5.00 | 5.00 |
| Cetyl Alcohol | 2.00 | 2.00 | 2.00 | 2.00 | 2.00 | 2.00 | 2.00 | 2.00 | 2.00 |
| Dimethylpolysiloxane | 1.25 | 1.25 | 1.25 | 1.25 | 1.25 | 1.25 | 1.25 | 1.25 | 1.25 |
| Glycerin | 12.00 | 12.00 | 12.00 | 12.00 | 12.00 | 12.00 | 12.00 | 12.00 | 12.00 |
| Benzyl Alcohol | 0.60 | 0.60 | 0.60 | 0.60 | 0.60 | 0.60 | 0.60 | 0.60 | 0.60 |
| Cyclopentasiloxane (and) PEG-12 Dimethicone Crossploymer | 4.00 | 4.00 | 4.00 | 4.00 | 4.00 | 4.00 | 4.00 | 4.00 | 4.00 |
| Alcohol (and) Water (and) *Acmella Oleracea* Extract* | — | 1.00 | — | 1.00 | 1.00 | 1.00 | 1.00 | 1.00 | 1.00 |
| *Mentha Arvensis* Leaf Oil (and) | — | — | 1.00 | 1.00 | — | — | — | — | — |

TABLE 1-continued

Formulation and Efficacy

| INCI Name | 1 | 2 | 3 | 4 | 5 | 6 | 7 | 8 | 9 |
|---|---|---|---|---|---|---|---|---|---|
| Citrus Medica Limonum (Lemon) Peel Oil (and) Cupressus Sempervirens Oil (and) Lavandula Hybrida Oil (and) Cistus ladanifer Oil** | | | | | | | | | |
| Mentha Arvensis Leaf Oil | — | — | — | — | 1.00 | — | — | — | — |
| Citrus Medica Limonum (Lemon) Peel Oil | — | — | — | — | — | 1.00 | — | — | — |
| Cupressus Sempervirens Oil | — | — | — | — | — | — | 1.00 | — | — |
| Lavandula Hybrida Oil | — | — | — | — | — | — | — | 1.00 | — |
| Cistus ladanifer Oil | — | — | — | — | — | — | — | — | 1.00 |
|  | 100.00 | 100.00 | 100.00 | 100.00 | 100.00 | 100.00 | 100.00 | 100.00 | 100.00 |
| Arachidonic Acid Methodology Results - 30 minutes | 0.075 ± 0.011 | 0.096 ± 0.009 | 0.074 ± 0.007 | 0.072 ± 0.010 | 0.094 ± 0.013 | 0.077 ± 0.012 | 0.074 ± 0.012 | 0.114 ± 0.028 | 0.075 ± 0.013 |
| % Reduction from Placebo | — | +28 | −1 | −4 | +25 | +3 | −10 | +52 | 0 |
| Arachidonic Acid Methodology Results - 60 minutes | 0.077 ± 0.013 | 0.095 ± 0.008 | 0.077 ± 0.015 | 0.065 ± 0.009 | 0.080 ± 0.013 | 0.093 ± 0.009 | 0.060 ± 0.016 | 0.083 ± 0.014 | 0.069 ± 0.009 |
| % Reduction from Placebo | — | +23 | 0 | −16 | +4 | +21 | −22 | +8 | −10 |

*= GATULINE EXPRESSION which contains *Acmella Oleracea* and is a source of spilanthol.
**= V-TONIC which is *Cupressus sempervirens* oil and may contain monoterpenes including α-pinene, limonene, 3-carene, α-terpinyl acetate, α-terpinolene, cedrol, γ-terpinene, and manoyle oxide.

*Cistus ladanifer* oil may contain monoterpenes including α-pinene, β-pinene, viridiflorol, bornyl acetate, 1,8-cineole, camphene, sabinene, myrcene, α-phellandrene, α-terpinene, γ-terpinene, limonene, p-cymene, 1,8-cineol, 2,2,6-trimethylcyclohexanone, fenchone, α-thujone, isomenthone, benzaldehyde, acetophenone, cis-citral, trans-citral, geranyl acetate, cis-3-hexen-1-ol, trans-2-hexen-1-ol, linalool, terpinen-4-ol, borneol, α-terpineol, nerol, geraniol, and eugenol.

Example 2

Neurosensory Model

Neurosensory inflammation, also referred to as neurogenic inflammation, is a type of inflammation triggered by sensory nerve activation in skin. Certain natural substances that act on vanilloid receptors cause sensory nerves (C-fibers) to release inflammatory neuropeptides such as substance P and calcitonin gene-related peptide. In mouse skin, an edema response occurs rapidly upon application of a vanilloid receptor activator, such as capsaicin or resiniferatoxin (RTX). Compounds that inhibit the response to neurosensory stimulation could be useful as topical analgesics, itch or sting inhibitors or soothing agents for irritated skin (see U.S. Pat. No. 6,090,811). We found unexpectedly that a combination of GATULINE EXPRESSION and V-TONIC inhibits the neurogenic inflammatory response to resiniferatoxin.

Albino male CD-1 mice, 7-9 weeks old, were used. Induction of neurogenic inflammation in the mouse ear was based on known methods (Inoue H, et al., Br J Pharmacol. 110:1614-1620, 1993). A 20-μl volume of Resiniferatoxin (0.05%) prepared in acetone was applied to the left ears (7 mice per treatment group). The right ear was not treated. Formulations containing the test agents were applied to the left ear (20 μL) immediately after resiniferatoxin challenge. The mice were sacrificed by $CO_2$ inhalation 30 minutes after applying the solutions. The left and right ears were removed and a 7-mm biopsy was removed from each ear and weighed. The difference in biopsy weights between the right and left ear was calculated. The percent inhibition was calculated by comparing treatments to resiniferatoxin alone. Anti-neurogenic inflammation effects of compounds are evident as an inhibition of the increase in ear weight. The results are shown in Table 2 below.

TABLE 2

| % GATULINE EXPRESSION | % V-TONIC | % Potassium LACTATE | % NEUTROL | SCORE |
|---|---|---|---|---|
| Lotion | | 1.0 | 1.0 | 27.96 |
| | | 2.5 | 2.5 | 41.86 |
| 2.0 | | | | 40.04 |
| 1.0 | | | | 33.86 |
| 0.8 | | | | 18.68 |
| 0.8 | 0.8 | | | 55.87 |
| 0.6 | 0.6 | | | 19.90 |
| | | 0.8 | | 0.73 |
| | | 1.0 | | 6.51 |

TABLE 2-continued

| % GATULINE EXPRESSION | % V-TONIC | % Potassium LACTATE | % NEUTROL | SCORE |
|---|---|---|---|---|
| | 2.0 | | | 31.23 |
| 0.8 | 0.1 | 1.0 | 1.0 | 30.8 |
| Cream | | 2.5 | 2.5 | 31.67 |
| 2.0 | | | | 27.25 |
| 1.0 | | | | 9.49 |
| 0.2 | 0.2 | | | −6.30 |
| 0.4 | 0.4 | | | 6.98 |
| 0.6 | 0.6 | | | 19.61 |
| 0.8 | 0.8 | | | 30.36 |
| 0.8 | 0.8 | 2.5 | 2.5 | 52.73 |
| | 0.8 | 2.5 | 2.5 | 31.23 |
| | 1.0 | | | −1.59 |
| | 2.0 | | | 9.32 |

This data demonstrates that extracts containing spilanthol in combination with extracts containing terpene compounds are synergistic in reducing edema and therefore are also effective at reducing associated pain and itch.

We claim:

1. A topical analgesic composition comprising:
   1% by weight of an extract of *Acmella oleracea*;
   1% by weight of one or more terpene-containing extract, wherein the terpene-containing extract is *Cistus ladanifer* oil, or *Cistus ladanifer* oil and *Cupressus sempervirens* oil; and a carrier.

2. The composition according to claim 1 which comprises an effective amount of the extract of *Acmella oleracea* and an effective amount of the one or more terpene-containing extract to inhibit a neurogenic inflammatory response to skin irritants.

3. The composition according to claim 1 wherein the terpene-containing extract comprises *Cistus ladanifer* oil.

4. The composition according to claim 1 wherein the terpene-containing extract is *Cistus ladanifer* oil and *Cupressus sempervirens* oil.

5. A topical lotion comprising the composition according to claim 1.

6. A topical analgesic composition comprising:
   an effective amount of an extract of *Acmella oleracea* and an effective amount of one or more terpene-containing extract, wherein the terpene-containing extract is *Cistus ladanifer* oil, or *Cistus ladanifer* oil and *Cupressus sempervirens* oil; and a carrier,
   wherein the extract of *Acmella oleracea* and the one or more terpene-containing extract are included in the composition in a 1:1 ratio by weight.

* * * * *